(12) United States Patent
Sorensen et al.

(10) Patent No.: US 11,045,354 B2
(45) Date of Patent: Jun. 29, 2021

(54) SELECTIVELY MOVEABLE VALVE ELEMENTS FOR ASPIRATION AND IRRIGATION CIRCUITS

(71) Applicant: Alcon Inc., Fribourg (CH)

(72) Inventors: Gary P. Sorensen, Mission Viejo, CA (US); Michael D. Morgan, Costa Mesa, CA (US); Mel Matthew Oliveira, Huntington Beach, CA (US)

(73) Assignee: Alcon Inc., Fribourg (CH)

( * ) Notice: Subject to any disclaimer, the term of this patent is extended or adjusted under 35 U.S.C. 154(b) by 213 days.

(21) Appl. No.: 16/428,116

(22) Filed: May 31, 2019

(65) Prior Publication Data

US 2019/0282401 A1    Sep. 19, 2019

Related U.S. Application Data

(63) Continuation of application No. 15/334,662, filed on Oct. 26, 2016, now Pat. No. 10,314,741, which is a continuation of application No. 13/685,860, filed on Nov. 27, 2012, now Pat. No. 9,561,321.

(60) Provisional application No. 61/568,220, filed on Dec. 8, 2011.

(51) Int. Cl.
*A61M 1/00* (2006.01)
*A61F 9/007* (2006.01)
*A61M 3/02* (2006.01)

(52) U.S. Cl.
CPC ...... *A61F 9/00745* (2013.01); *A61F 9/00736* (2013.01); *A61M 1/008* (2013.01); *A61M 1/0031* (2013.01); *A61M 1/0033* (2014.02); *A61M 3/0279* (2013.01); *A61M 3/0283* (2013.01); *A61B 2217/005* (2013.01); *A61B 2217/007* (2013.01); *A61M 1/0058* (2013.01); *A61M 3/0241* (2013.01); *A61M 3/0258* (2013.01); *A61M 2205/128* (2013.01); *A61M 2210/0612* (2013.01)

(58) Field of Classification Search
CPC ............ A61F 9/00736; A61M 1/0058; A61M 2210/0612; A61M 3/0283; A61M 1/00
See application file for complete search history.

(56) References Cited

U.S. PATENT DOCUMENTS

2009/0163853 A1    6/2009    Cull

*Primary Examiner* — Deanna K Hall

(57) ABSTRACT

Various arrangements of fluidics systems are disclosed. In one arrangement, an aspiration circuit for a fluidics system is disclosed that selectively controls aspiration. The aspiration circuit comprises an aspiration line operatively connected to a surgical instrument, an aspiration exhaust line operatively connected to a waste receptacle; an aspiration vent line connected at a first end to the aspiration line; and a selectively variable vent valve operatively connected to the aspiration vent line. The variable vent valve may be selectively moved to vary aspiration pressure within the aspiration line. Other fluidics systems are disclosed that include a selectively positionable irrigation valve that may also be incorporated into a fluidics system that includes a variable vent valve.

18 Claims, 16 Drawing Sheets

SELECTIVELY MOVEABLE VALVE ELEMENTS FOR ASPIRATION AND IRRIGATION CIRCUITS

PRIORITY CLAIM

This application:

(a) is a continuation of U.S. patent application Ser. No. 15/334,662, titled "SELECTIVELY MOVEABLE VALVE ELEMENTS FOR ASPIRATION AND IRRIGATION CIRCUITS", filed on Oct. 26, 2016, whose inventors are Gary P. Sorensen and Michael D. Morgan, which is a continuation of U.S. patent application Ser. No. 13/685,860, titled "SELECTIVELY MOVEABLE VALVE ELEMENTS FOR ASPIRATION AND IRRIGATION CIRCUITS", filed on Nov. 27, 2012, whose inventors are Gary P. Sorensen, Michael D. Morgan, and Mel M. Oliveira, and (b) claims the benefit of priority of U.S. Provisional Patent Application Ser. No. 61/568,220 (U.S. patent application Ser. Nos. 15/334,662 and 13/685,860 claimed the benefit of priority of provisional application Ser. No. 61/568,220, titled "SELECTIVELY MOVEABLE VALVE ELEMENTS FOR ASPIRATION AND IRRIGATION CIRCUITS", filed on Dec. 8, 2011, whose inventors are Gary P. Sorensen, Michael D. Morgan, and Mel M. Oliveira).

All three of the above applications are hereby incorporated by reference in their entirety as though fully and completely set forth herein.

TECHNICAL FIELD

The present disclosure relates generally to surgical systems and methods. More specifically, the present disclosure relates to systems and methods for controlling fluid flow in aspiration and/or irrigation circuits during a surgical procedure using one or more selectively moveable valve elements.

BACKGROUND

The human eye functions to provide vision by transmitting light through a clear outer portion called the cornea, and focusing the image by way of the lens onto the retina. The quality of the focused image depends upon many factors including the size and shape of the eye, and the transparency of the cornea and lens.

When age or disease causes the lens to become less transparent, vision deteriorates because of the diminished light which can be transmitted to the retina. This deficiency in the lens of the eye is known as a cataract. Ophthalmic surgery is required for treating this condition. More specifically, surgical removal of the deteriorated lens and replacement with an artificial intraocular lens (IOL).

One known technique for removing cataractous lenses is phacoemulsification. During this procedure, a thin phacoemulsification cutting tip is inserted into the diseased lens and vibrated ultrasonically. The vibrating cutting tip liquefies or emulsifies the lens so that the diseased lens may be aspirated out of the eye. Once removed, an artificial lens is inserted therein.

A typical ultrasonic surgical device suitable for ophthalmic procedures includes an ultrasonically driven handpiece, an attached cutting tip, an irrigation sleeve and an electronic control console. The handpiece assembly is attached to the control console by an electric cable and flexible tubing. Through the electric cable, the console varies the power level transmitted by the handpiece to the attached cutting tip and the flexible tubing supplies irrigation fluid to, and draws aspiration fluid from, the eye through the handpiece assembly.

The operative part of the handpiece includes a hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece. The handpiece body terminates in a reduced diameter portion or nosecone at the body's distal end. The nosecone accepts the irrigation sleeve. Likewise, the horn bore receives the cutting tip. The cutting tip is adjusted so that the tip projects only a predetermined amount past the open end of the irrigating sleeve.

In use, the ends of the cutting tip and irrigating sleeve are inserted into a small incision of predetermined size in the cornea, sclera, or other location of the eye. The cutting tip is ultrasonically vibrated along its longitudinal axis within the irrigation sleeve by the crystal-driven ultrasonic horn, thereby emulsifying the selected tissue in situ. A hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, through the cutting tip and horn bores and through the aspiration line, into a collection device. The aspiration of emulsified tissue is aided by a saline flush solution or irrigant that is injected into the surgical site through a small annular gap between the inside surface of the irrigating sleeve and the cutting tip.

Known phacoemulsification systems may even use a surgical cassette to provide a variety of functions for vitreoretinal surgical procedures to assist with effectively managing irrigation and aspiration flows into and out of the surgical site through the surgical device. More specifically, the cassette acts as the interface between surgical instrumentation and the patient and delivers pressurized irrigation and aspiration flows into and out of the eye. A variety of pumping systems have been used in connection with a surgical cassette in fluidics systems for cataract surgery, including positive displacement systems (most commonly, peristaltic pumps) and vacuum based aspiration sources. A peristaltic system uses a series of rollers acting upon an elastomeric conduit to create flow in the direction of rotation, while vacuum based systems employ a vacuum source, typically applied to the aspiration flow through an air-liquid interface.

During surgical procedures, the hollow, resonating tip can become occluded with tissue. In such an instance, vacuum can build in the aspiration line downstream of the occlusion. When the occlusion eventually breaks apart, this pent up vacuum can, depending upon vacuum level and the amount of aspiration path compliance, draw a significant amount of fluid from the eye, thereby increasing the risk of anterior chamber shallowing or collapse. This situation is commonly referred to as occlusion break surge.

To address this concern, surgical consoles are configured with sensors in the aspiration path to allow detection of vacuum level and limiting of vacuum by the system to a predetermined maximum level. While limiting the maximum vacuum level in such a manner may be effective to reduce the potential magnitude of an occlusion break surge, such limitations on the maximum vacuum level can reduce effectiveness of lens removal and increase overall surgical time. In some systems, an audible indication of relative vacuum level and/or vacuum reaching the user preset limit may be provided so that the surgeon can take appropriate precautions.

For example, in some systems, vacuum is commonly relieved upon a command from the surgeon to open a vent valve that connects the aspiration line to a pressure source that is maintained at or above atmospheric pressure. Depending upon the system, this might be the irrigation line, the pump exhaust line or a line connected to atmospheric air (air venting system). However, there are some concerns with known vent valves. First, known vent valves are only configured for simple "on/off" action. For example, pinched tubing valves or elastomer dome type valves may provide satisfactory on/off control of fluid flow but do not exhibit consistent variable flow characteristics. As such, this type of valve has a very sharp surge recovery curve. Moreover, the configuration of dome type valves also may present operational challenges. For example, the operation of the valve is highly dependent upon the elastomer material to obtain a proper seat position, thus consistency of the material is very important. Further, the flow through the valve may also become clogged by debris if the opening formed by the elastomer is small. In addition, such a configuration may undesirably trap air bubbles. Use of these type of valves is also limited in that due to the nature of the on/off flow control limitation, an array of valves are need to support directing fluid flow from one circuit to another.

Alternatively, vacuum may be reduced or relieved by reversal of the pump rotation in positive displacement systems. While it is known to employ a system having bi-directional pump rotation to allow control of pressure/vacuum level based on user input and feedback from a pressure sensor in the aspiration line, such a system requires rapid acceleration and deceleration of the pump head mass. This can limit response time and cause objectionable acoustical noise.

Known cassettes used with consoles also allow the aspiration line to be vented, either to atmosphere or to a liquid so as to reduce or eliminate vacuum surge upon occlusion break. Prior art air vented cassettes allow ambient air to enter the aspiration line, however, venting air into the aspiration line changes the fluidic performance of the aspiration system by greatly increasing aspiration path compliance. Increased compliance can significantly increase the magnitude of occlusion break surge and also negatively affect system responsiveness. Liquid venting systems allow irrigation fluid to bleed into the aspiration line, thereby reducing any impact on the fluidic performance of the aspiration system. When higher aspiration vacuums are used, cassettes that vent the aspiration line to the irrigation line can cause high pressure surges in the irrigation line. Other systems provide a separate source of irrigation fluid to vent the aspiration line, requiring the use of two irrigation fluid sources and increasing the cost and complexity of the system.

BRIEF SUMMARY

Various arrangements of fluidics systems are disclosed. In one exemplary arrangement, an aspiration circuit for a fluidics system is proposed that selectively controls aspiration. For example, one exemplary aspiration circuit comprises an aspiration line operatively connected to a surgical instrument, an aspiration exhaust line operatively connected to a waste receptacle; an aspiration vent line connected at a first end to the aspiration line; and a selectively variable vent valve operatively connected to the aspiration vent line. The variable vent valve may be selectively actuated to vary aspiration pressure within the aspiration line. In another exemplary arrangement, the variable vent valve is configured as a multi-purpose valve that can vary aspiration pressure and selectively interrupt irrigation fluid flow. In yet another exemplary arrangement, the variable vent valve is configured as a multi-purpose valve that can vary aspiration pressure, as well as direct aspiration from either a displacement-based and/or vacuum-based aspiration source.

BRIEF DESCRIPTION OF THE DRAWINGS

Exemplary embodiments of the present disclosure will now by described by way of example in greater detail with reference to the attached figures, in which.

DETAILED DESCRIPTION

Figure 1:
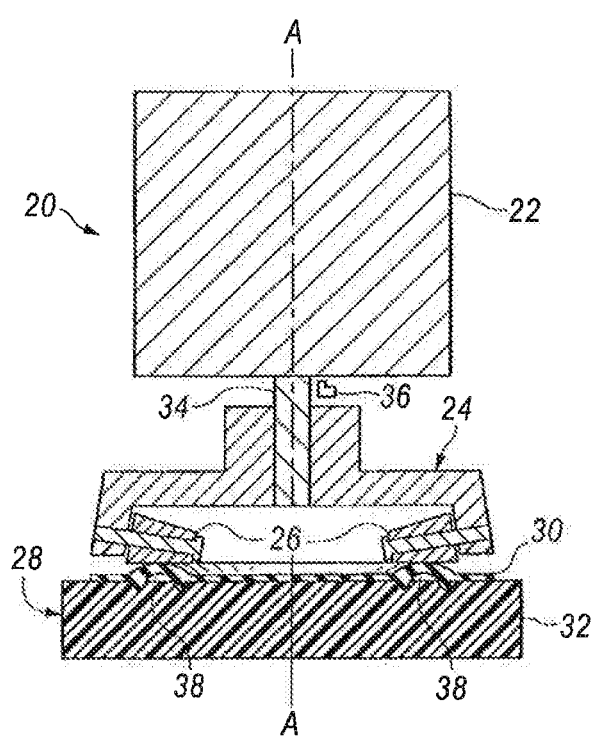
FIG. 1 is a cross-sectional view of an exemplary arrangement of a peristaltic pump used in a phacoemulsification machine for ophthalmic procedures.

Referring now to the discussion that follows and also to the drawings, illustrative approaches to the disclosed devices and methods are shown in detail. Although the drawings represent some possible approaches, the drawings are not necessarily to scale and certain features may be exaggerated, removed, or partially sectioned to better illustrate and explain the present disclosure. Further the descriptions set forth herein are not intended to be exhaustive or otherwise limit or restrict the claims to the precise forms and configurations shown in the drawings and disclosed in the following detailed description.

Phacoemulsification machines are typically used in cataract eye surgery to remove cataract-affected eye lenses, such machines typically employ fluidics systems for introducing irrigative fluid into the surgical site, as well as providing aspiration from the surgical site to remove emulsified tissue. In some known systems a positive displacement system, such as a pump, is employed to provide appropriate aspiration. Referring to FIG. 1, an exemplary arrangement of a pump 20 for a phacoemulsification system is shown. Pump 20 includes a pump motor 22 and a roller head 24 containing one or more rollers 26. Pump 20 may be used in combination with a cassette 28 having an elastomeric sheet 30 applied to the exterior of a relatively rigid body or substrate 32. Pump motor 22 may be a stepper or DC servo motor. Roller head 24 is attached to a shaft 34 of pump motor 22 such that pump motor 22 rotates roller head 24 in a plane generally perpendicular to the axis A-A of shaft 34. Shaft 34 may also contain a shaft position encoder 36.

Sheet 30 of cassette 28 contains a fluid channel 38 that may be molded therein, channel 38 being configured to be generally planar and arcuate in shape (within the plane). Fluid channel 38 has a radius approximating that of rollers 26 about shaft 34.

Figure 2:
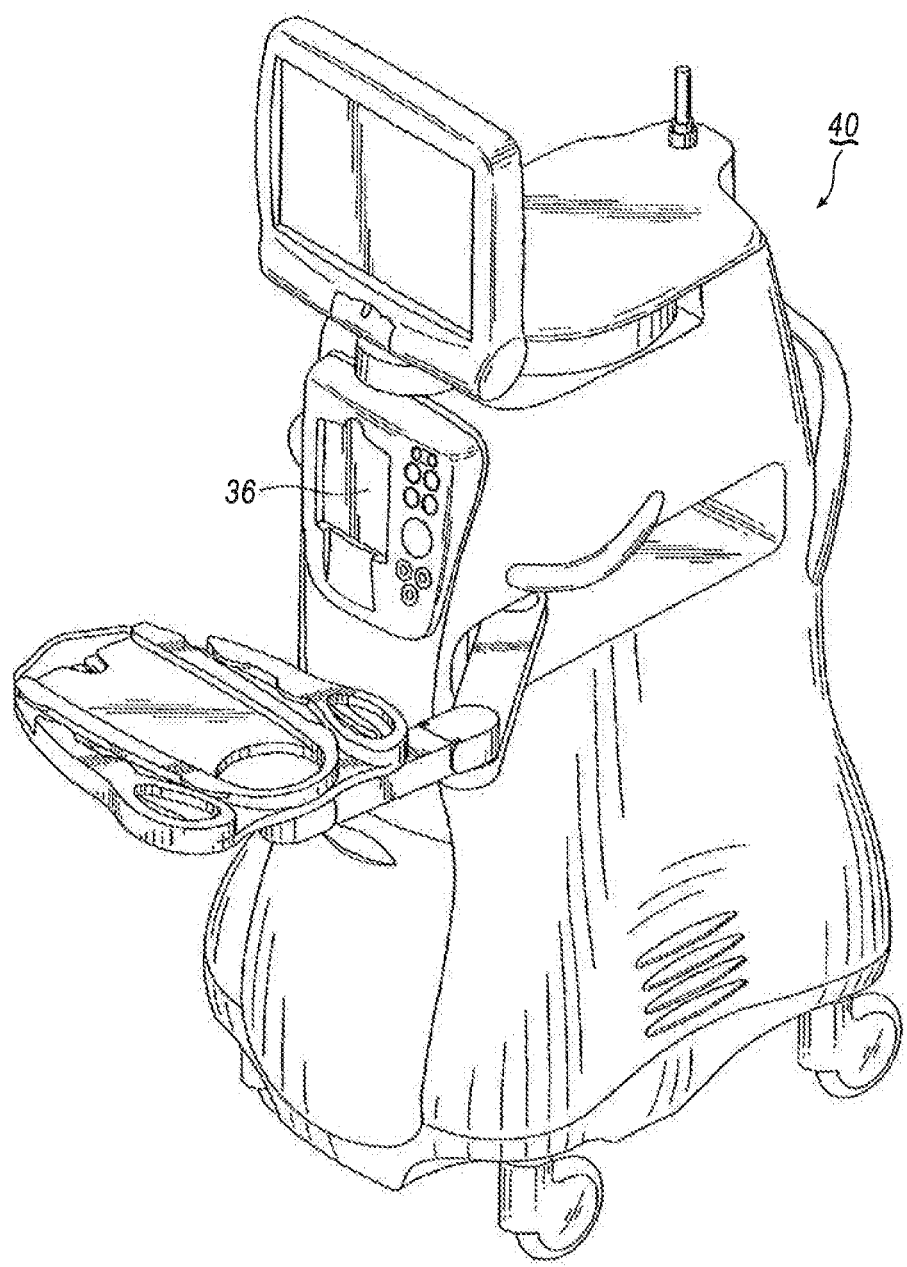
FIG. 2 is a perspective view of a surgical console that may be used in a phacoemulsification machine.
Figure 3:
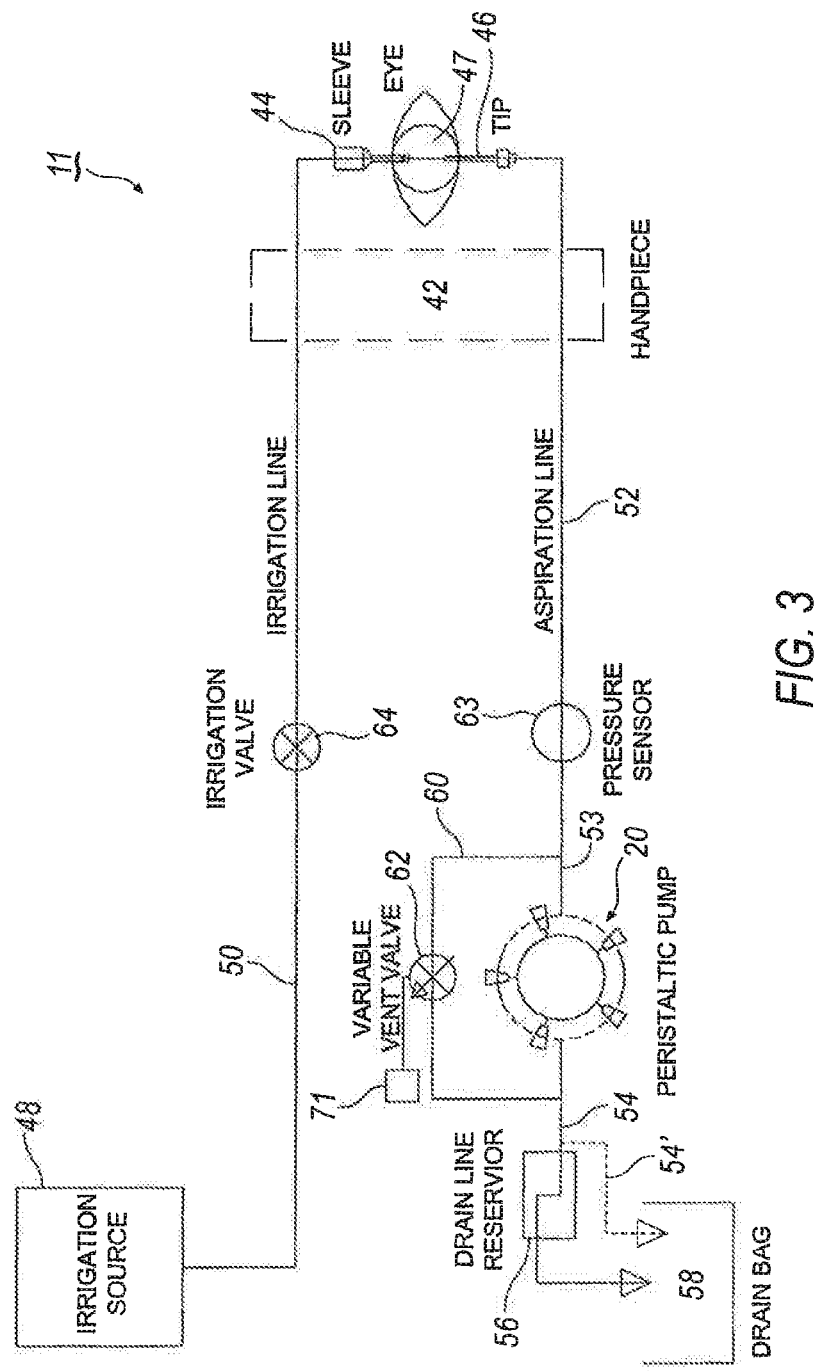
FIG. 3 is a schematic diagram of an exemplary arrangement of a phaco fluidics system for a phacoemulsification machine having selectively variable vent valve disposed between an aspiration line and an aspiration exhaust line.

Cassette 28 is designed to be mounted in a cassette receiver 36 of a console 40 (as shown in FIG. 2). Cassette 28 operatively couples console 40 to a handpiece 42 (an exemplary schematic arrangement of handpiece 42 is shown in FIG. 3). Handpiece 42 generally includes an infusion sleeve 44 and a tip member 46, whereby tip member 46 is positioned coaxially within infusion sleeve 44. Tip member 46 is configured for insertion into an eye 47. Infusion sleeve 44 allows irrigation fluid to flow from console 40 and/or cassette 28 into the eye. Aspiration fluid may also be withdrawn through a lumen of tip member 46, with console 40 and cassette 28 generally providing aspiration/vacuum to tip member 46. Collectively, the irrigation and aspiration functions of phacoemulsification system 10 are hereby referred to as a phaco fluidics system 11.

Referring now to FIG. 3, an exemplary phaco fluidics system 11 will be described for use with a positive displacement system (i.e., pump 20). Infusion sleeve 44 of handpiece 42 is connected to an irrigation source 48, which contains an irrigation fluid, by suitable tubing (i.e., irrigation line 50). In one exemplary arrangement, irrigation source 48 may be a pressurized irrigation source (e.g., a bag of irrigation fluid that is selectively compressed to deliver irrigation fluid to an irrigation supply line). Tip member 46 is connected to an input port 53 of a pump, such as pump 20, by a length a suitable tubing (i.e., aspiration line 52).

An aspiration exhaust line 54 extends from pump 20. In one exemplary arrangement, aspiration exhaust line 54 is fluidly connected to a drain line reservoir 56. Reservoir 56 may also drain into an optional drain bag 58. Alternatively, as shown in phantom, exhaust line 54' may be fluidly connected directly to drain bag 58.

An aspiration vent line 60 is fluidly connected between aspiration line 52 and aspiration exhaust line 54. Vent line 60 is configured as a bypass circuit. A vent valve 62, to be discussed in further detail below, is fluidly connected to aspiration vent line 60 so as to selectively control the aspiration pressure within aspiration line 52. A pressure sensor 63 is also in fluid communication with aspiration line 52 to detect aspiration pressure within aspiration line 52. Pressure sensor 63 is also operatively connected to a control system in console 40. The control system may be configured to provide pre-set aspiration pressure levels for fluidics system 11, as will be explained below in further detail.

As described above, irrigation source 48, which may be pressurized, is fluidly connected to handpiece 42 by irrigation line 50. An irrigation valve 64 is fluidly connected to and positioned between irrigation line 50 and infusion sleeve 44. Irrigation valve 64 provides selective on/off control of irrigation fluid in irrigation line 50.

Vent valve 62 is configured to provide a variable orifice size within vent line 60 to selectively modulate aspiration within aspiration line 52. More specifically, use of a variable vent valve 62 enables unidirectional rotation of pump 20 in a first direction to generate flow/vacuum, while permitting a mechanism for dynamically controlling aspiration pressure to handpiece 42. In one exemplary vent valve 62 may be configured as a multi-position rotary type valve that would allow predictable and precise control of the orifice size based on angular position of vent valve 62 within vent line 60.

Figure 4:
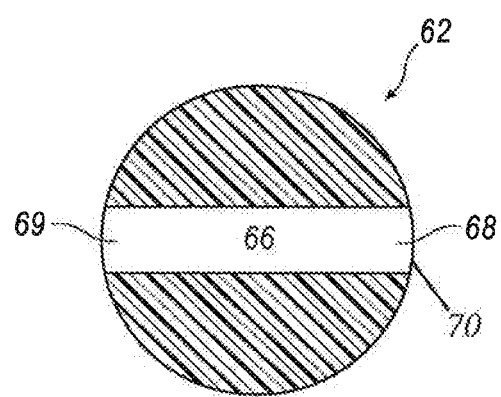
FIG. 4 is a cross-sectional view of an exemplary configuration of a variable vent valve for use in a phaco fluidics system.

An exemplary configuration of vent valve 62 is shown in FIG. 4. In FIG. 4, in one exemplary configuration, multi-position vent valve 62 includes a channel 66 defined by first and second openings 68 and 69. While channel 66 is shown in FIG. 4 as being generally uniformly sized from first opening 68 to second opening 69, it is understood that channel 66 may be configured with a variable size. For example, first 68 and second openings 69 may be configured with a diameter that is larger than a central portion of channel 66 such that first and second openings 68 and 69 flare outwardly toward a periphery 70 of vent valve 62.

In operation, vent valve 62 is selectively rotatable in an aspiration circuit, such that the angular position of channel 68 is selectively moveable within vent line 60. Such movement may full open, partially occlude, and/or completely occlude, first and second opening 68 and 69 so as to selectively control the aspiration pressure within aspiration line 52.

Pressure sensor 63 is operably connected to a control system mounted in console 40. Pressure sensor 63 detects and communicates pressure changes in aspiration line 52 during operation of the phacoemulsification machine. In one exemplary configuration, predetermined pressure thresholds can be set within the control system such that when pressure readings from pressure sensor 63 exceed those thresholds, the control system may selectively modify the aspiration pressure within aspiration line 52. For example, if the pressure sensor 63 detects that the aspiration pressure has exceed the predetermined pressure threshold, console 40 triggers movement of vent valve 62 within vent line 60 by a predetermined amount to permit venting of aspiration line 52 sufficient to drop the aspiration pressure below the pre-set threshold. Thus, pressure sensor 63, vent valve 62 and the control system cooperate to permit real-time modulation of aspiration within aspiration line 52 which permits a higher maximum aspiration level to be utilized, but still providing effective occlusion break surges.

For example, referring back to FIG. 3, channel 66 of vent valve 62 is positioned such that first and second openings 68 and 69 are positioned out of alignment with vent line 60. In this position, vent valve 62 is in a "fully closed" position thereby blocking vent line 60 and providing unimpeded aspiration pressure to aspiration line 52. If pressure sensor 63 detects that aspiration pressure has increased within aspiration line 52 above the threshold level, vent valve 62 may be selectively moved by a predetermined amount so as to move first and second openings 68 and 69 into at least partial alignment, thereby partially opening aspiration exhaust line 54/54'. This action quickly and effectively restores the aspiration pressure within aspiration line 52 to a predetermined acceptable amount, without requiring pump reversal. However, it is understood that due to the configuration of channel 66, a variety of aspiration pressures may be achieved by selective movement of the vent valve 62.

Vent valve 62 is operably connected to an actuator, such as a motor 71, having an angular position encoder (such as encoder 36). One such exemplary motor 71 includes a stepper motor. When pressure sensor 63 detects that aspiration pressure has exceed a predetermined threshold, the controller may automatically operate motor 71 to rotate vent valve 62 to a predetermined angular position, thereby quickly changing aspiration pressure within aspiration line 52. Further, the controller, in cooperation with a pressure sensor positioned in irrigation line 50, may be configured to detect and minimize an occlusion break onset. More specifically, vent valve 62 may be automatically rotated by motor 71 to reduced aspiration pressure within aspiration line 52. This function would operate to lessen an effect of a post occlusion break surge. Because vent valve 62 permits selective and dynamic control of aspiration levels within aspiration line 52, vacuum levels may be easily modulated for the user's preference, thereby providing quicker and more efficient lens removal.

Figure 5:
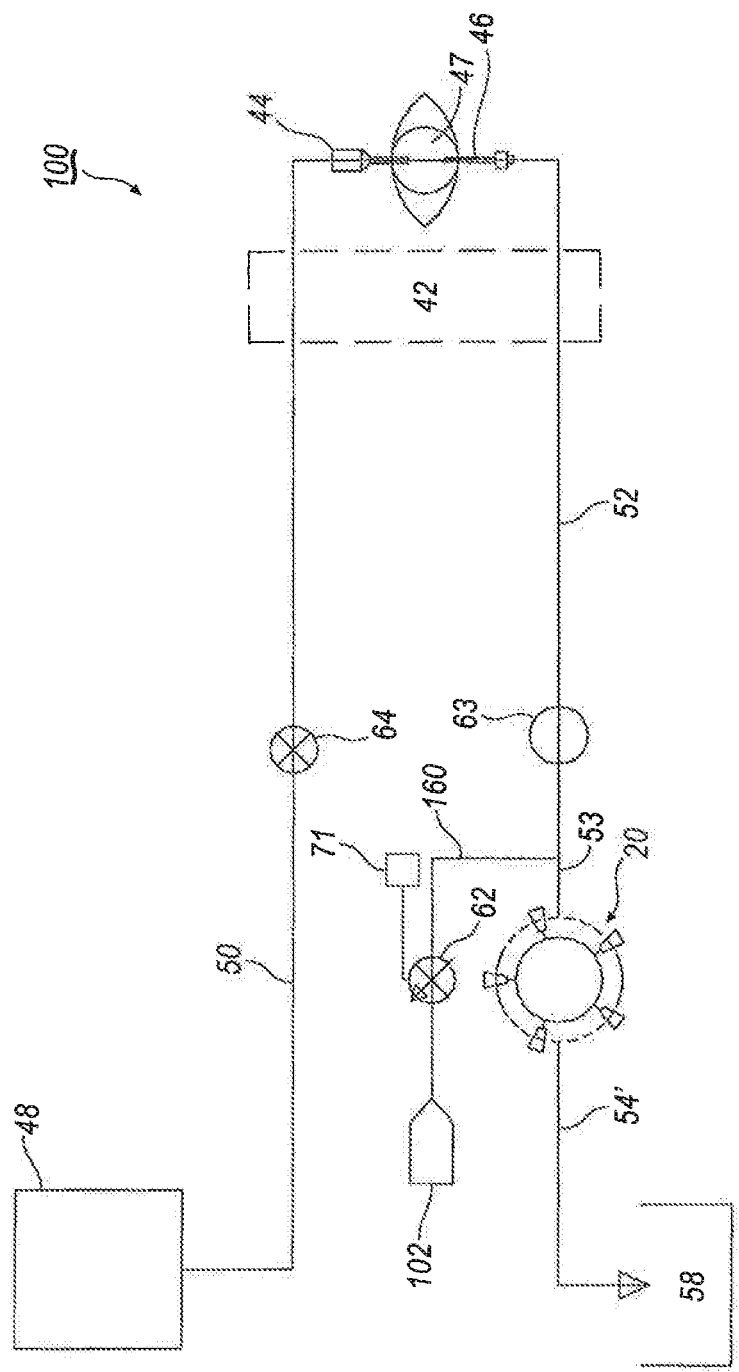
FIG. 5 is a schematic diagram of an exemplary arrangement of a phaco fluidics system for a phacoemulsification machine having selectively variable vent valve disposed between an aspiration line and atmosphere.

Referring now to FIG. 5, components of an alternative exemplary phaco fluidics system 100 for use with a positive displacement pumping system is shown. Phaco fluidics system 100 includes many of the same components as shown and described above in connection with FIG. 3. Accordingly, like components have been given the same reference numbers. For a description of those components, reference is made to the discussion above with respect to FIG. 3.

In phaco fluidics system 100, an aspiration exhaust line 54' extends from pump 20 and is fluidly connected to a drain bag 58. Alternatively, as shown in FIG. 3, phaco fluidics system 100 may include an exhaust line 54 that is fluidly connected to a drain line reservoir.

An aspiration vent line 160 is fluidly connected between aspiration line 52 and atmosphere 102. A variable vent valve 62 is fluidly connected to aspiration vent line 160 so as to selectively control the aspiration pressure within aspiration line 52. Pressure sensor 63 is also in fluid communication with aspiration line 52.

As discussed above, vent valve 62 is configured to provide a variable orifice size to selectively modulate vacuum, thereby allowing unidirectional rotation of pump 20 to generate flow/vacuum, while permitting selective control of vacuum/aspiration to handpiece 42 based on angular position of vent valve 62. Vent valve 62 is configured to be selectively rotatable to dynamically control aspiration within aspiration line 52.

As discussed above, in operation, pressure sensor 63 is operably connected to a control system mounted in console 40. Pressure sensor 63 detects and communicates pressure changes in aspiration line 52 during operation of the phacoemulsification machine. In one exemplary configuration, predetermined pressure thresholds are set by the users within the control system. Accordingly, when pressure sensor 63 detects an aspiration pressure level that exceeds the pre-set thresholds, the control system moves vent valve 62 by a predetermined amount to reduce the aspiration pressure within aspiration line 52 by positioning channel 66 in vent valve 62 in at least partial communication with atmosphere 102. It is also understood that vent valve 62 may be fully opened to atmosphere 102 to effectively fully vent aspiration line 52. It is also understood that vent valve 62 may be selectively moved to fully close vent line 160 to atmosphere 102, thereby effectively providing full vacuum/aspiration pressure in aspiration line 52 to tip member 46. Movement of vent valve 62 to selectively adjust the aspiration pressure within aspiration line 52 may be accomplished either manually (e.g., selective operation of a footswitch treadle based on prior user settings) or automatically by motor 71 that is operatively connected to the control system.

Figure 6:
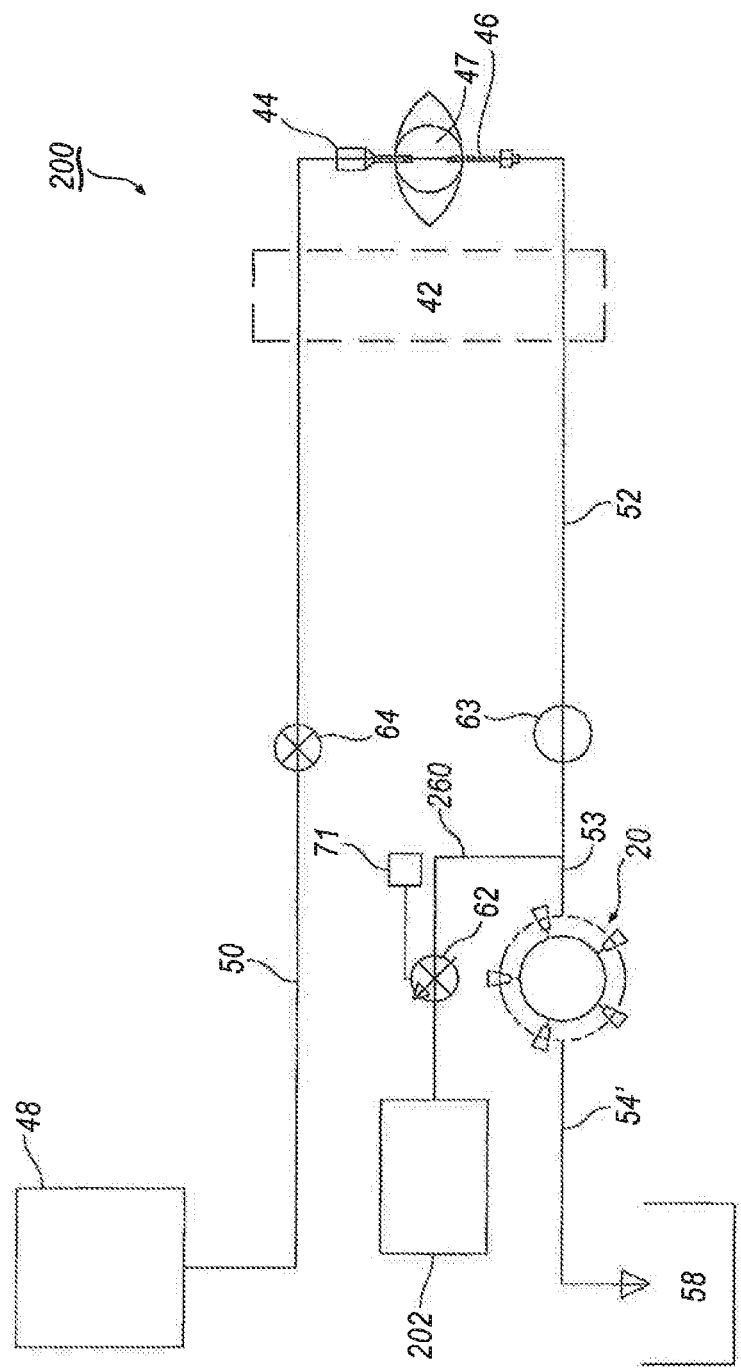
FIG. 6 is a schematic diagram of an exemplary arrangement of a phaco fluidics system for a phacoemulsification machine having selectively variable vent valve disposed between an aspiration line and a vent pressure source.

Referring now to FIG. 6, components of another alternative exemplary phaco fluidics system 200 for use with a positive displacement pumping system is shown. Phaco fluidics system 200 includes many of the same components as shown and described above in connection with FIGS. 3 and 5. Accordingly, like components have been given the same reference numbers. For a detailed discussion of those components, reference is made to the discussion above with respect to FIG. 3.

An aspiration vent line 260 is fluidly connected between aspiration line 52 and a vent pressure source 202. Examples of suitable vent pressure sources include, but are not limited to, a pressurized fluid or saline. Variable vent valve 62 is fluidly connected to aspiration vent line 260 so as to selectively control the aspiration pressure within aspiration line 52. Pressure sensor 63 is also in fluid communication with aspiration line 52.

Vent valve 62 is configured to provide a variable orifice size to selectively modulate vacuum, thereby allowing unidirectional rotation of pump 20 in a first direction to generate flow/vacuum, while permitting selective control of vacuum/aspiration to handpiece 42 based on the angular position of vent valve 62.

Pressure sensor 63 is operably connected to a control system mounted in console 40 and detects and communicates pressure changes in aspiration line 52 during operation of the phacoemulsification machine. In one exemplary configuration, predetermined pressure thresholds are set within the control system such that when pressure readings from pressure sensor 63 exceed those thresholds, vent valve 62 is moved by a predetermined amount to reduce the aspiration pressure within aspiration line 52. This is accomplished by positioning channel 66 in vent valve 62 in at least partial communication with a vent pressure source 202, thereby opening vent line 260, and permitting pressurized fluid (for example) to enter into aspiration line 52. Motor 71 may be operably connected to vent valve 62 to automatically move vent valve 62 by a predetermined amount to automatically control the level of vacuum/aspiration pressure in aspiration line 52 based on information received from sensor 63. It is also understood that vent valve 62 may be fully opened to vent pressure source 202 to effectively negate aspiration pressure in aspiration line 52, without need to interrupt pump 20 operation. Alternatively, it is also understood that vent valve 62 may be fully closed, i.e., channel 66 being positioned completely out of alignment with vent line 260, such that vent pressure source 202 is not in communication with vent line 260. This configuration effectively provides full vacuum/aspiration pressure in aspiration line 52 to tip member 46.

Figure 7:
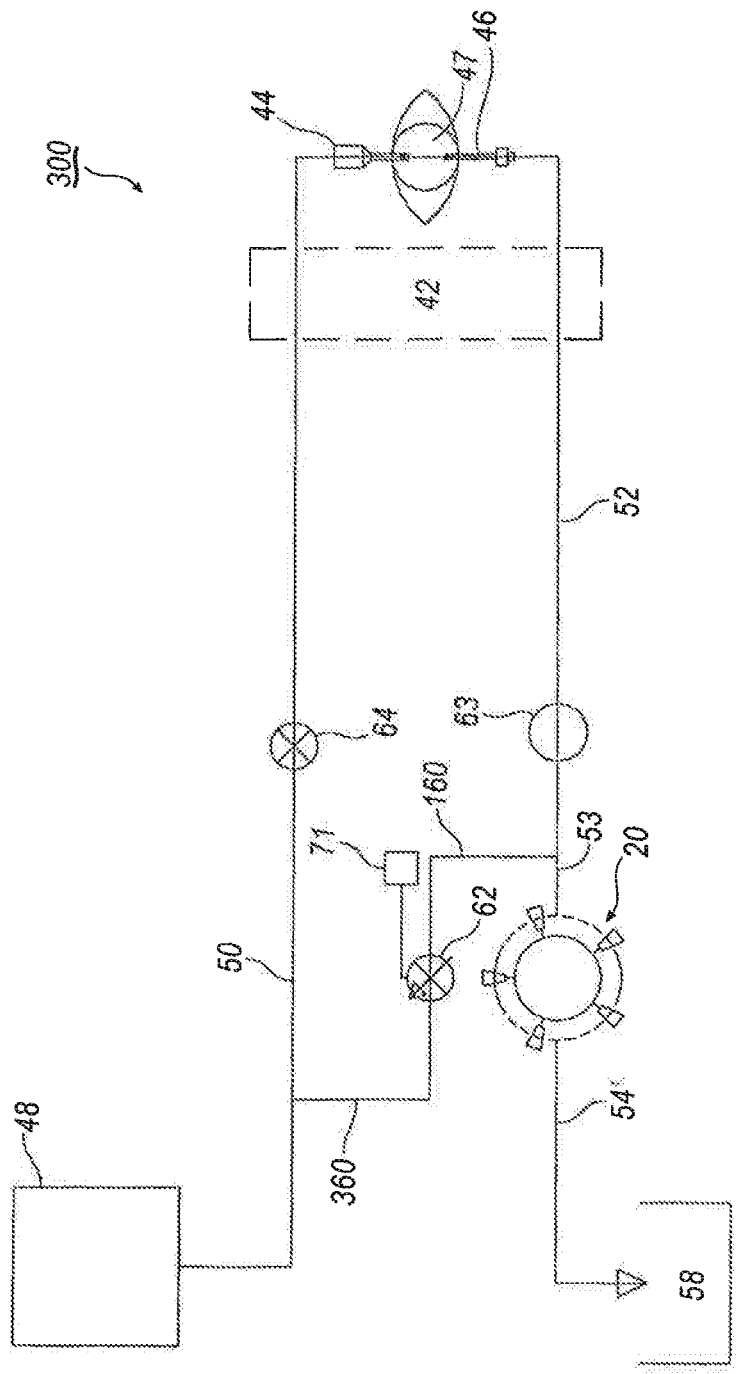
FIG. 7 is a schematic diagram of an exemplary arrangement of a phaco fluidics system for a phacoemulsification machine having selectively variable vent valve disposed between an aspiration line and an irrigation line.

Referring now to FIG. 7, components of a yet another alternative exemplary phaco fluidics system 300 for use with a positive displacement pumping system is shown. Phaco fluidics system 300 includes many of the same components as shown and described above in connection with FIGS. 3 and 5-6. Accordingly, like components have been given the same reference numbers. For a detailed discussion of those components, reference is made to the discussion above with respect to FIG. 3.

An aspiration vent line 360 is fluidly connected between aspiration line 52 and irrigation line 50. Variable vent valve 62 is fluidly connected to aspiration vent line 360 so as to selectively control the aspiration pressure within aspiration line 52. A pressure sensor 63 is also in fluid communication with aspiration line 52.

Vent valve 62 is configured to provide a variable orifice size to selectively modulate vacuum, thereby allowing uninterrupted unidirectional rotation of pump 20 in a first direction to generate flow/vacuum, while permitting selective control of vacuum/aspiration to handpiece 42 based on angular position of vent valve 62.

Pressure sensor 63 is operably connected to a control system mounted in console 40 and detects and communicates pressure changes in aspiration line 52 during operation of the phacoemulsification machine. In one exemplary configuration, predetermined pressure thresholds are set within the control system such that when pressure readings from pressure sensor 63 exceed those thresholds, vent valve 62 may be selectively moved by a predetermined amount to reduce, for example, the aspiration pressure within aspiration line 52. For example, channel 66 in vent valve 62 is moved so as to be in at least partial alignment with vent line 360, thereby placing aspiration line 52 in at least partial communication with irrigation line 50 by a predetermined amount to automatically control the level of vacuum/aspiration pressure in aspiration line 52 based on information received from sensor 63. It is understood that vent valve 62 may be fully opened to irrigation line 50 to effectively negate aspiration pressure in aspiration line 52. Alternatively, it is also understood that vent valve 62 may be positioned so as to fully close irrigation line 50, thereby effectively providing full vacuum/aspiration pressure in aspiration line 52 to tip member 46. In such a configuration, channel 66 is fully aligned with vent line 360.

Figure 8:
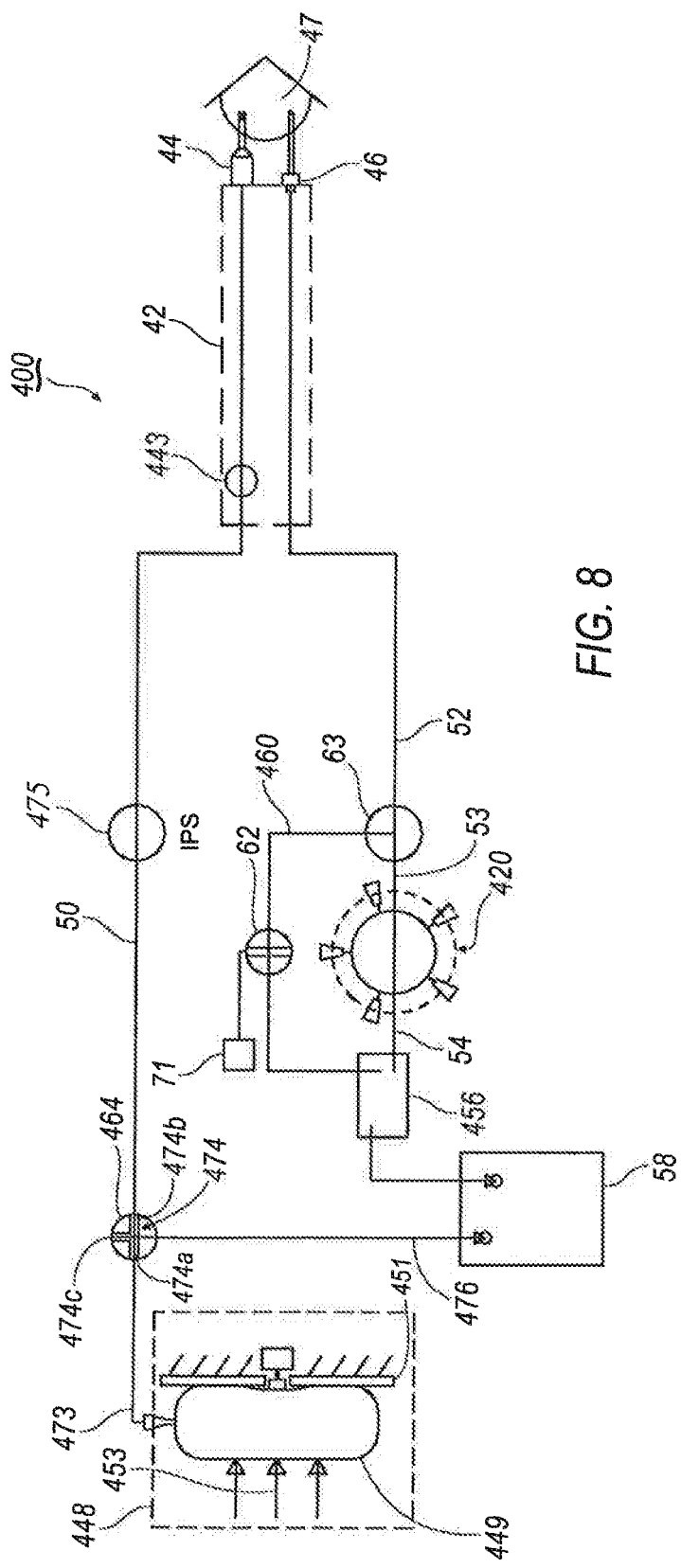
FIG. 8 is a schematic diagram of an exemplary arrangement of a phaco fluidics system for a phacoemulsification machine having selectively variable vent valve disposed between an aspiration line and an aspiration exhaust line, and a multi-position irrigation valve.

Referring now to FIG. 8, components of yet another alternative exemplary phaco fluidics system 400 for use with a positive displacement pumping system is shown. Phaco fluidics system 400 includes many of the same components as shown and described above in connection with FIGS. 3 and 5-7.

Phaco fluidics system 400 includes infusion sleeve 44 of handpiece 42 that is connected to an irrigation source 448 by irrigation line 50. Phaco fluidics system 400 may also include a multi-position irrigation valve 464 that is fluidly connected to and positioned at a three-way junction between an irrigation supply line 473, irrigation line 50 and a shunt line 476. An irrigation line pressure sensor 475 may be positioned in irrigation line 50 between shunt line 476 and infusion sleeve 42. Handpiece 42 may also be provided with a handpiece pressure sensor 443.

While irrigation source 448 may be any suitable irrigation source, in one exemplary arrangement, irrigation source 448 is pressurized. More specifically, an irrigation bag 449 may be provided that is positioned against a platform 451 and a pressurizing force, represented by arrows 453, is applied to irrigation bag 449 so as to force infusion fluid out of irrigation bag 449 and into irrigation supply line 473. Other pressurized fluid systems are also contemplated.

Tip member 46 is connected to input port 53 of a peristaltic pump 420 by aspiration line 52. While any suitable pump arrangement may be utilized, in one exemplary configuration, pump 420 is a pump such as described in U.S. Patent Application Publication No. 20100286651, entitled "Multiple Segmented Peristaltic Pump and Cassette" or a pump such as described in U.S. Pat. No. 6,962,488, entitled "Surgical Cassette Having an Aspiration Pressure Sensor, the contents of both of which are incorporated by reference in their entirety. Aspiration exhaust line 54 extends from pump 420 and is fluidly connected to a vent reservoir 456. Vent reservoir 546 is fluidly connected to a drain bag 58.

An aspiration vent line 460 is fluidly connected between aspiration line 52 and vent reservoir 456, so as to bypass pump 420. Variable vent valve 62 is fluidly connected to aspiration vent line 460 so as to selectively control the aspiration pressure within aspiration line 52. An aspiration pressure sensor 63 is also in fluid communication with aspiration line 52. Vent valve 62 is configured to provide a variable orifice size within vent line 460 to selectively modulate vacuum, thereby allowing unidirectional rotation of pump 420 in a first direction to generate flow/vacuum, while permitting selective control of vacuum/aspiration to handpiece 42 based on the angular position of vent valve 62.

In operation, pressure sensor 63 is operably connected to a control system mounted in console 40. Pressure sensor 63 detects and communicates pressure changes in aspiration line 52 during operation of the phacoemulsification machine. In one exemplary configuration, predetermined pressure thresholds are set within the control system such that when pressure readings from pressure sensor 63 exceed those thresholds, vent valve 62 may be selectively moved by a predetermined amount to reduce the aspiration pressure within aspiration line 52. This is accomplished by positioning channel 66 in vent valve 62 in at least partial communication with vent line 460. Because vent line 460 is operably connected to vent reservoir 456, the partial communication of channel 66 with vent line 460 effectively reduces aspiration pressure within aspiration line 52. Movement of vent valve 62 may be accomplished by motor 71 that is connected to vent valve 62. More specifically, motor 71 may be configured to automatically move vent valve 62 by a predetermined amount to automatically control the level of vacuum/aspiration pressure in aspiration line 52 based on information received from sensor 63. It is understood that vent valve 62 may be oriented to a fully opened position to fully vent aspiration line to vent reservoir 456 to effectively close off input port 53 to pump 420. Alternatively, it is also understood that vent valve 62 may be fully closed, i.e., such that channel 66 is out of alignment with vent line 460, thereby closing vent reservoir 456 to aspiration line 52, thereby effectively providing full vacuum/aspiration pressure in aspiration line 52 to tip member 46.

Figure 9A:
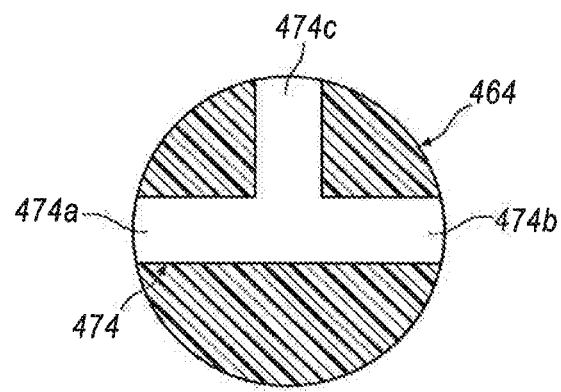
FIG. 9A is a cross-sectional view of an exemplary irrigation valve for use in the phaco fluidics system of FIG. 8.

As stated above, phaco fluidics system 400 also provides a multi-position irrigation valve 464 that is positioned at a junction between irrigation supply line 473, irrigation line 50 and shunt line 476. As explained in further detail below, irrigation valve 464 is configured as a rotary valve that may be operatively positioned to selectively control irrigation in phaco fluidics system 400. As shown in FIG. 9A, in one exemplary arrangement, multi-position irrigation valve 464 includes an intersecting channel configuration 474. More specifically, channel 474 includes a first branch 474A, a second branch 474B and a third branch 474C. While shown as having a T-shaped configuration, it is understood that other intersecting configuration may be utilized, depending on the configuration of the various fluid lines in fluidics system 400.

In operation, as shown in FIG. 8, when irrigation valve 464 is oriented such that first branch 474A is fully aligned with irrigation supply line 473 and third branch 474B is fully aligned with irrigation line 50, but second branch 474C is oriented out of alignment with shunt line 476, normal, full irrigation flow is provided to irrigation line 50. However, to prime irrigation supply 448 of phaco fluidics system 400, irrigation valve 464 may be selectively rotated such that first branch 474A is fully aligned with shunt line 476 and third branch 474C is fully aligned with irrigation supply line 473. Accordingly, when phaco fluidics system 400 is operated, fluid from irrigation supply 448 is directed to drain bag 58. To prime irrigation pressure sensor 475, irrigation valve 464 may be selectively rotated such that second arm 474B is fully aligned with shunt line 476 and third arm 474C is fully aligned with irrigation line 50.

While the various branches of irrigation valve 464 shown in FIG. 8 has been described as operating so as to be fully aligned with either the irrigation line 50, shunt line 476 and irrigation supply line 473, it is also understood that branches 474a-474c need not be fully aligned with the respective lines 50, 476, and 473. Indeed, irrigation valve 464 may be configured to be selectively positioned so as to effectively control the amount of fluid to be delivered to eye 47. Indeed, in some patients, a full irrigation flow (such a shown in FIG. 8), may lead to patient discomfort, while a controlled opening whereby certain branches of irrigation valve 464 is positioned at various angular positions with respect to irrigation line 50 may be desirable. Thus, similar to vent valve 62, irrigation valve 464 may also be configured for variable irrigation delivery.

Figure 9B:
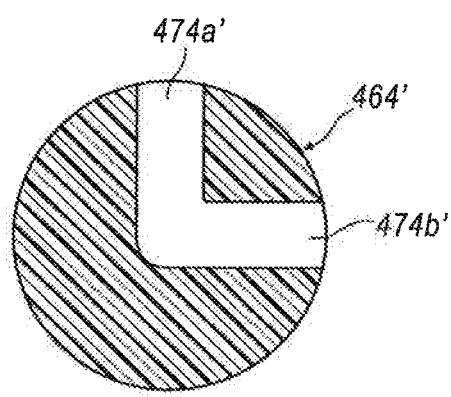
FIG. 9B is a cross-sectional view of an alternative exemplary irrigation valve for use in a phaco fluidics system.

Another alternative configuration for a multi-position irrigation valve is shown in FIG. 9B. In this arrangement, a multi-position irrigation valve 464' is provided having an L-shaped pathway formed therein. Multi-position irrigation valve 464' includes a first branch 474A' and a second branch 474B'. Use of multi-position irrigation valve 464' will be described below in connection with FIGS. 10A-10C.

Figure 10A:
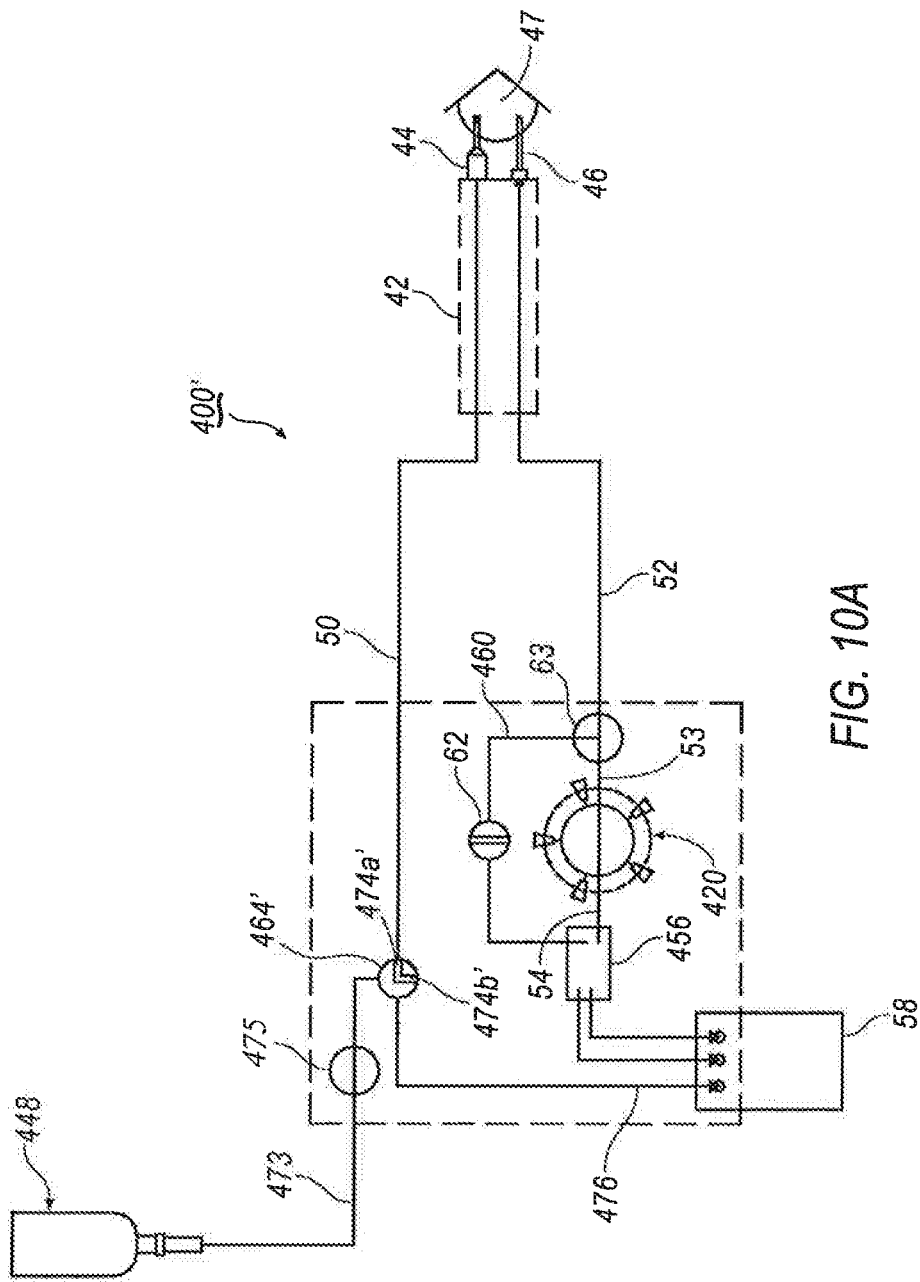
FIG. 10A is a schematic diagram of an exemplary arrangement of a phaco fluidics system for a phacoemulsification machine incorporating the multi-position irrigation valve of FIG. 9B in an "off" position.
Figure 10B:
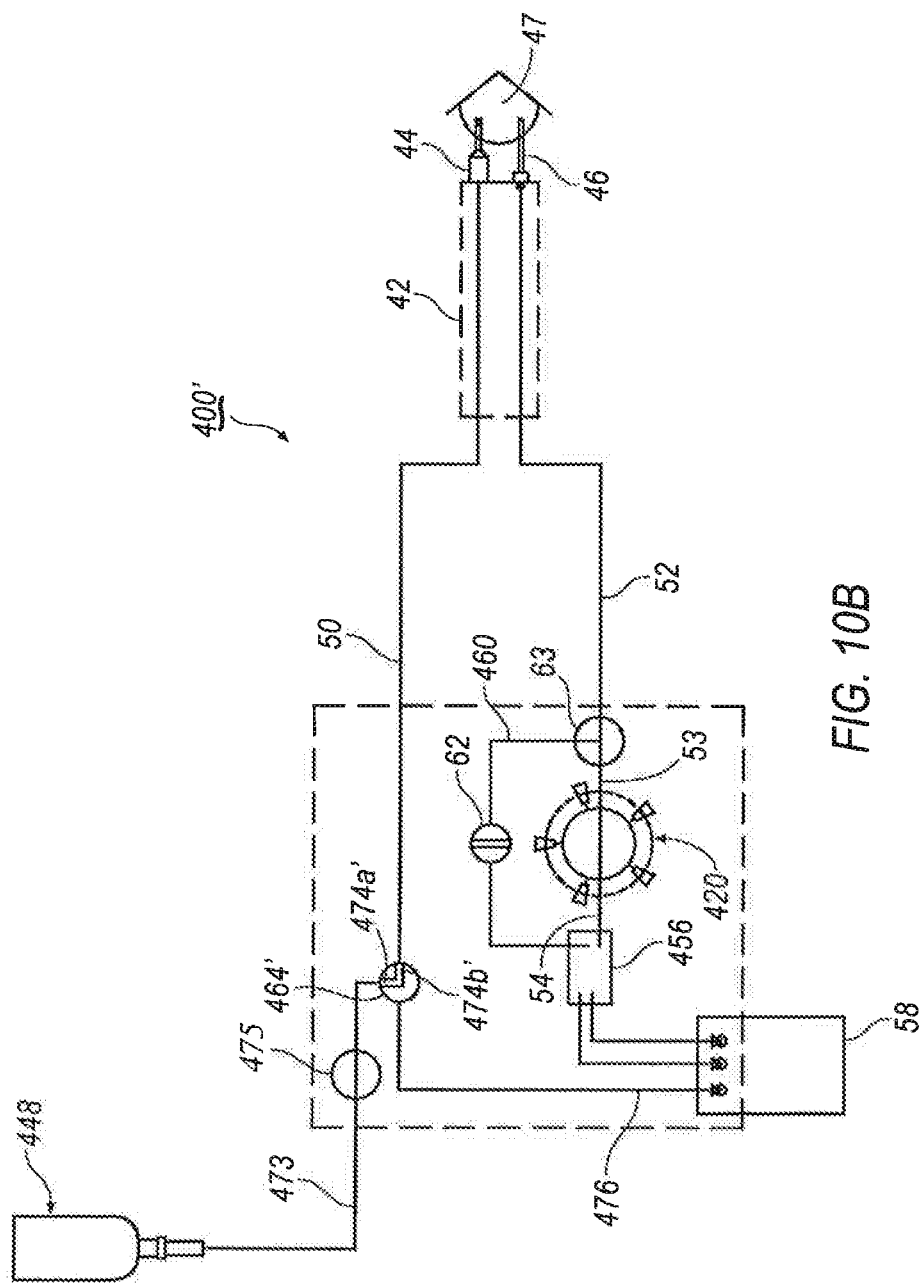
FIG. 10B is a schematic diagram of an exemplary arrangement of a phaco fluidics system for a phacoemulsification machine incorporating the multi-position irrigation valve of FIG. 9B in an "irrigation" position.
Figure 10C:
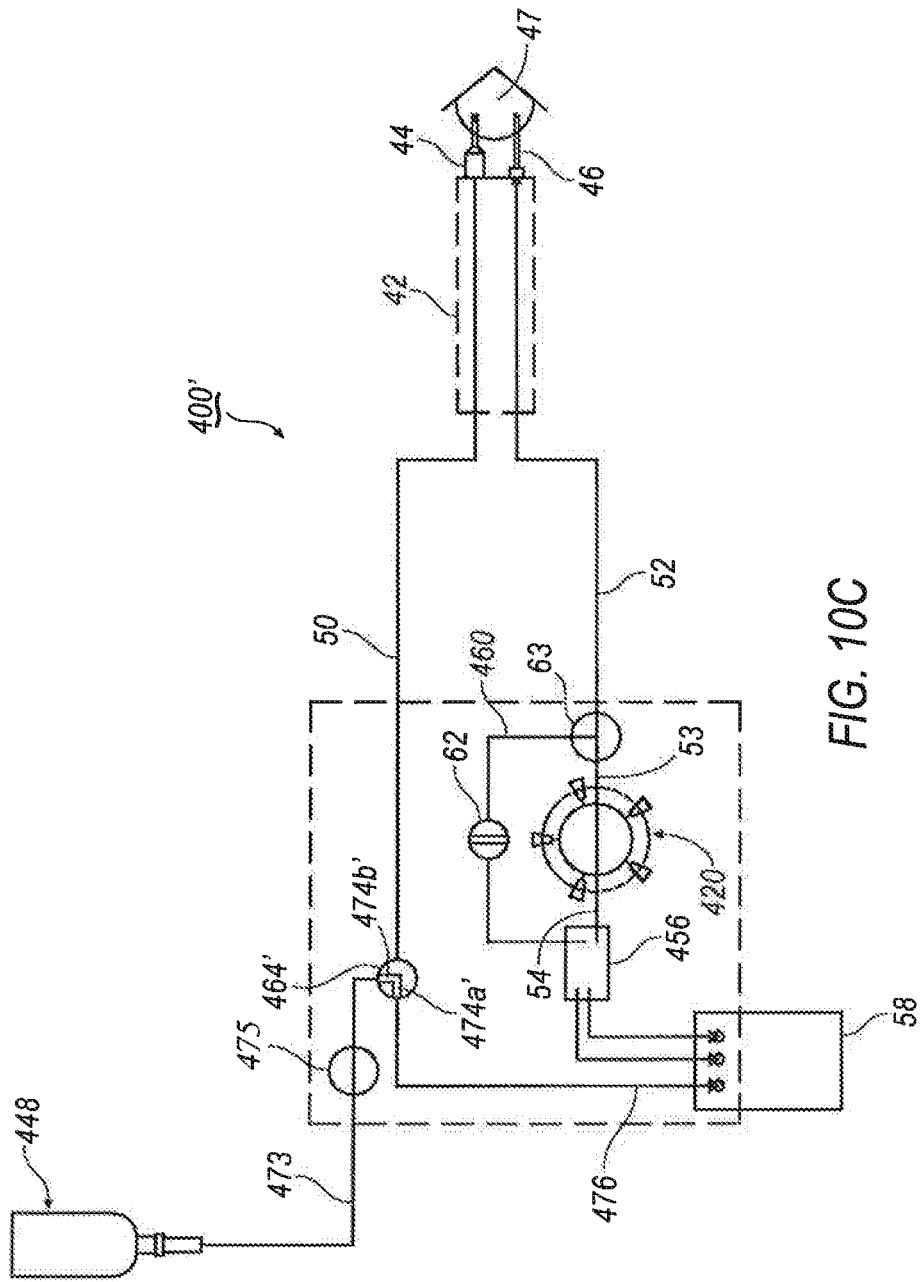
FIG. 10C is a schematic diagram of an exemplary arrangement of a phaco fluidics system for a phacoemulsification machine incorporating the multi-position irrigation valve of FIG. 9B in a "shunt" position.

Referring to FIGS. 10A-10C, components of another alternative exemplary phaco fluidics system 400' for use with a positive displacement pumping system is shown. Phaco fluidics system 400' includes many of the same components as shown and described above in connection with FIGS. 3 and 5-8. In some embodiments, the components inside of the dashed box may at least partially be included in a fluidics cassette configured to be secured to a surgical console.

Phaco fluidics system 400' includes infusion sleeve 44 of handpiece 42 that is connected to an irrigation source 448 by irrigation line 50. A multi-position irrigation valve 464' is fluidly connected to and positioned at a three-way junction between an irrigation supply line 473, irrigation line 50 and a shunt line 476. An irrigation line pressure sensor 475 may be positioned in irrigation line 50 between irrigation supply 448 and handpiece 42. While irrigation source 448 may be any suitable irrigation source, in one exemplary arrangement, irrigation source 448 includes an irrigation container that utilizes gravity to force infusion fluid out of the irrigation container and into irrigation supply line 473.

Multi-position irrigation valve 464' may be configured as a rotary valve that may be operatively positioned to selective control irrigation in phaco fluidics system 400'. Thus, in operation, as shown in FIG. 10A, when irrigation valve 464' is oriented such that first branch 474A' is aligned with irrigation line 50 and second branch 474B' is oriented so as to be out of alignment with irrigation supply line 473 and shunt line 476, no irrigation is supplied to irrigation line 50.

Referring now to FIG. 10B, to supply irrigation to handpiece 42, irrigation valve 464' may be selectively rotated such that first branch 474A' is at least partially aligned with irrigation supply line 473 and second branch 474B' is at least partially aligned with irrigation line 50. Accordingly, fluid from irrigation supply 448 is directed through irrigation supply line 473, to irrigation line 50 through irrigation valve 464' and to handpiece 42. As with irrigation valve 464, it may be desirable to selectively position first and second branches 474A' and 474B' so as to effectively control the amount of fluid to be delivered to eye 47. Thus, it is contemplated that irrigation line 50 may be subject to a controlled opening with irrigation supply line 473, whereby first and second branches 474A' and 474B' of irrigation valve 464' is positioned at various angular positions to provide less than full irrigation flow through irrigation line 50. Thus, similar to vent valve 62, irrigation valve 464' may also be configured for variable irrigation delivery.

FIG. 10C illustrates a priming operation for irrigation supply 448 of phaco fluidics system 400' by actuation of irrigation valve 464'. More specifically, irrigation valve 464' may be selectively rotated such that first branch 474A' is at least partially aligned with shunt line 476 and second branch 474B' is at least partially aligned with irrigation supply line 473. Accordingly, when phaco fluidics system 400 is operated, fluid from irrigation supply 448 is directed to drain bag 58.

While multi-position irrigation valves 464 and 464' have both been described in connection with a phaco fluidics system 400 that also incorporates a variable vent valve 62, it is understood that the scope of the present disclosure is not limited to a phaco fluidics system 400 that includes both a multi-position irrigation valve 464/464' and a variable vent valve 62. Further, multi-position irrigation valves 464/464' are capable of operating in an "on/off" type fashion, or, as described above, multi-position irrigation valves 464/464' may also be configured to provide a variable orifice so as to selectively control the amount of irrigation, in a manner similar to that which has been previously described in connection with variable vent valve 62. For example, the amount of irrigation to be provided to handpiece 42 from irrigation supply line 473 may be selectively controlled by a multi-position variable irrigation line, such that less than full irrigation from irrigation supply line 473 may be supplied to irrigation line 50 (and thus handpiece 42). In such an instance, multi-position variable irrigation valve 464/464' is selectively rotated so as to provide only partial communication with both irrigation supply line 473 and irrigation line 50.

Figure 11:
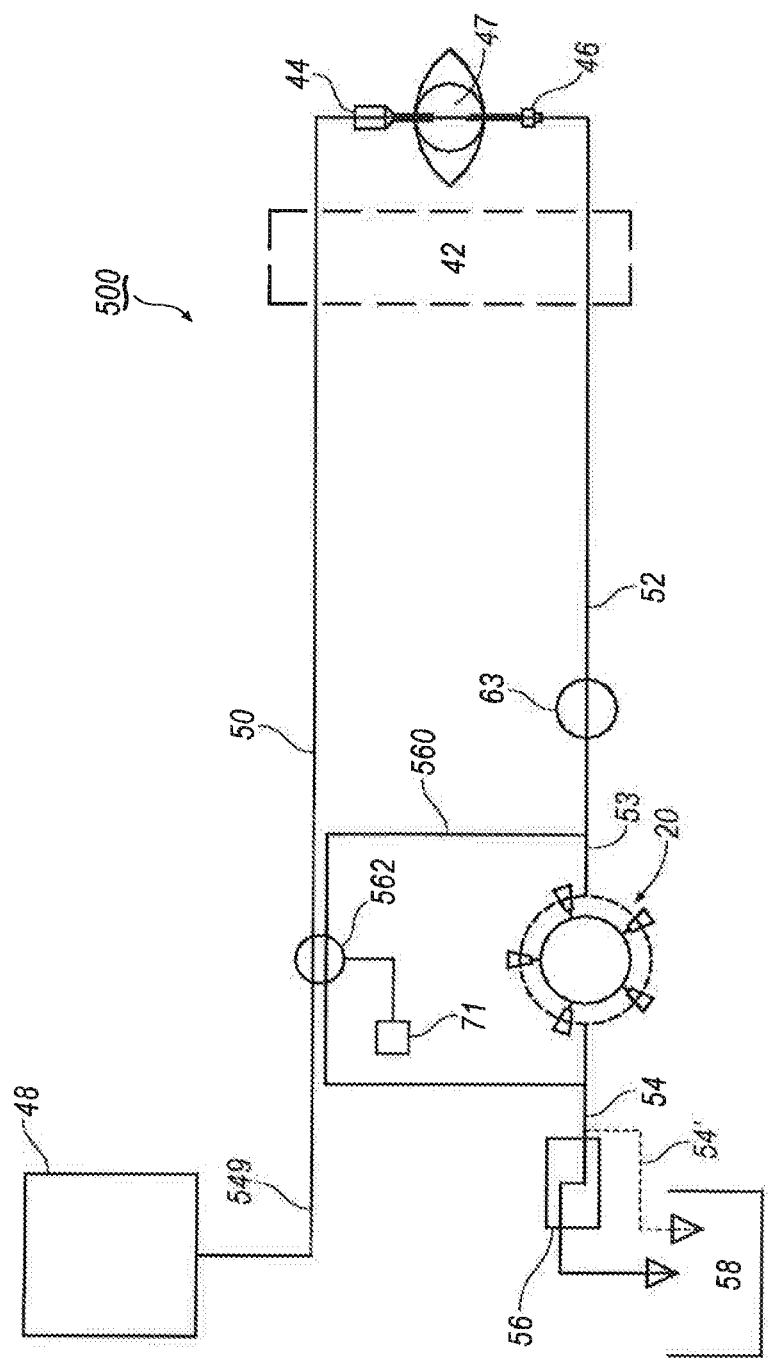
FIG. 11 is a schematic diagram of an exemplary arrangement of a phaco fluidics system for a phacoemulsification machine having a multi-purpose valve disposed between an aspiration line and an irrigation line.

Referring now to FIG. 11, components of a yet another alternative exemplary phaco fluidics system 500 for use with a positive displacement pumping system is shown. Phaco fluidics system 500 includes many of the same components as shown and described above in connection with FIGS. 3, and 5-10. Accordingly, like components have been given the same reference numbers. For a detailed discussion of those components, reference is made to the discussion above with respect to FIG. 3.

Phaco fluidics system 500 includes infusion sleeve 44 of handpiece 42 that is connected to irrigation source 48 by an irrigation supply line 549 that is fluidly connected to an irrigation line 50. An aspiration exhaust line 54 extends from pump 20. In one exemplary arrangement, aspiration exhaust line 54 is fluidly connected to a drain line reservoir 56. Reservoir 56 may also drain into an optional drain bag 58. Alternatively, as shown in phantom, exhaust line 54' may be fluidly connected directly to drain bag 58.

An aspiration vent line 560 is fluidly connected between aspiration line 52 and irrigation line 50. A multi-purpose proportional valve 562 is fluidly connected between aspiration vent line 560 and irrigation line 50 so as to selectively control the aspiration pressure within aspiration line 52 and irrigation flow within irrigation line 50. Pressure sensor 63 is also in fluid communication with aspiration line 52.

Figure 12A:
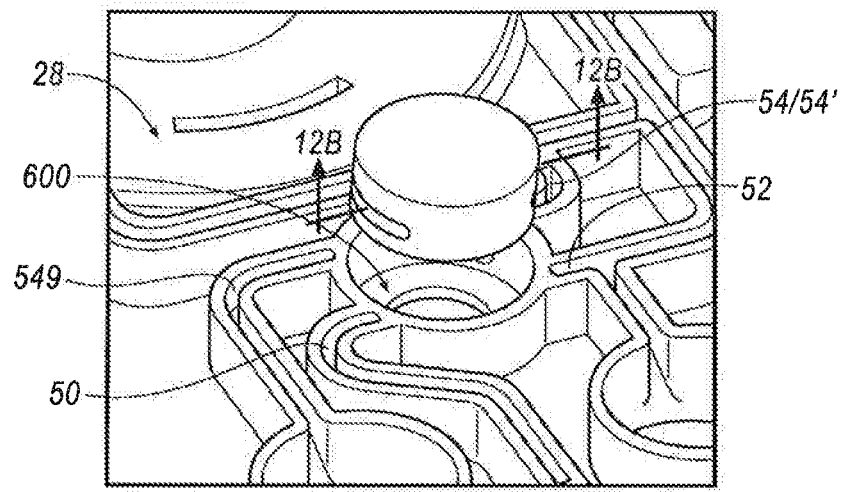
FIG. 12A is a partially exploded perspective view of an exemplary multi-purpose valve and a surgical cassette for use in the phaco fluidics system of FIG. 11.
Figure 12B:
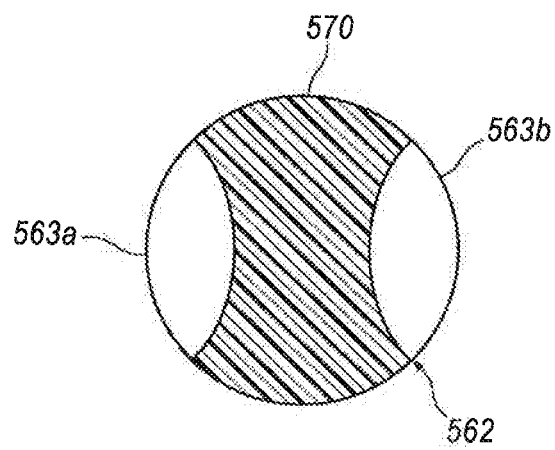
FIG. 12B is a cross-sectional view of the multi-purpose valve taken along lines 12B-12B in FIG. 12A.

Multi-purpose valve 562 is configured to provide a variable orifice size to selectively modulate aspiration, thereby allowing unidirectional rotation of pump 20 in a first direction to generate flow/vacuum, while permitting selective control of vacuum/aspiration to handpiece 42 based on the angular position of multi-purpose valve 62, as well as providing irrigation control. More specifically, in one exemplary configuration, referring to FIGS. 12A-12B, the body of multi-purpose valve 562 is defined by a periphery 570. The body has a first flow path 563A formed in one portion of the periphery 570 and a second flow path 563B formed in another portion of the periphery 570.

Referring back to FIG. 12A, in operation, multi-purpose valve 562 is selectively rotatable within a groove 600 formed in cassette 28. More specifically, operably connected to groove 600 are a plurality of fluid lines that are selectively connectable to one another via the angular position of multi-purpose valve 562. For example, in phaco fluidics system 500 shown in FIG. 11, multi-purpose valve 562 serves to operatively connect irrigation supply line 549, irrigation line 50, aspiration line 52 and aspiration exhaust line 54/54' via first and second flow paths 563A, 563B. Multi-purpose valve 562 is moveable within groove 600 so as to provide a variety of connection arrangements with respect to aspiration line 52, irrigation line 50, irrigation supply line 549 and aspiration exhaust line 54/54' may be achieved, as will be explained in further detail below.

Pressure sensor 63 is operably connected to a control system mounted in console 40 and is configured to detect and communicate pressure changes in aspiration line 52 during operation of the phacoemulsification machine. In one exemplary configuration, predetermined pressure thresholds are set within the control system such that when pressure readings from pressure sensor 63 exceed those thresholds, the control system may selectively move multi-purpose valve 562 by a predetermined amount to reduce the aspiration pressure within aspiration line 52. More specifically, second flow path 563B in multi-purpose valve 562 is moveable with respect to aspiration vent line 560.

For example, multi-purpose valve 562 may be positioned within groove 600 and selectively rotated such that second flow path 563B fully closes aspiration vent line 560 off from aspiration line 52, such that full vacuum, as dictated by the user's pre-selected pressure settings, is provided. However, if pressure has increased within aspiration line 52 by an undesirable amount (such as, for example, because of an occlusion break surge), multi-purpose valve 562 may be selectively moved by a predetermined amount such that second flow path 563B operatively connects aspiration line 54/54' directly to aspiration line 52, via aspiration vent line 560, thereby bypassing pump 20. This action quickly and effectively restores the aspiration pressure within aspiration line 52 to the predetermined acceptable amount, without requiring pump reversal.

In one exemplary arrangement, multi-purpose valve 562 may be operably connected to a footswitch treadle. Accordingly, the user may operate the footswitch treadle to rotate multi-purpose valve 562 to selectively vent (e.g., by lifting his/her foot from the treadle) aspiration line 52. The footswitch treadle may be configured to rotate multi-purpose valve 562 by a predetermined amount and in a predetermined direction, based on the control system settings, based on user input. Due to the configuration of second flow path 563B, a variety of aspiration pressures may be achieved by selective movement of multi-purpose valve 562. In some exemplary situations, it may be desirable to fully open exhaust line 54/54', thereby fully venting aspiration line 52.

In another exemplary arrangement, multi-purpose valve 562 is operably connected to a motor 71, such as a stepper motor, having an angular position encoder (such as encoder 36). When pressure sensor 63 detects that aspiration pressure has exceed a predetermined threshold, the controller automatically operates motor 71 to rotate multi-purpose valve 562 to a predetermined position, thereby quickly changing aspiration pressure within aspiration line 52. As the controller, in cooperation with pressure sensor 63, may be configured to detect an occlusion break onset, multi-purpose valve 562 may be automatically rotated by motor 71 to reduced aspiration pressure within aspiration line 52 below predetermined settings. This function would operate to lessen the post occlusion surge. Because multi-purpose valve 562 permits selective and dynamic control of aspiration levels within aspiration line 52, higher vacuum rates may be selected and employed by the user for quicker and more efficient lens removal.

In addition to selectively controlling the aspiration levels within the system 500, multi-purpose valve 562 also serves an additional purpose, namely controlling irrigation through irrigation line 50. More specifically, first flow path 563A is configured to selectively connect irrigation supply line 549 to irrigation line 50 when first flow path 563A is in communication with both irrigation supply line 549 and irrigation line 50. However, multi-purpose valve 562 may be selectively rotated such that first flow path 563A is placed out of communication with irrigation supply line 549, thereby effectively closing off irrigation.

Moreover, the configuration of multi-purpose valve 562 also permits the selective control of the aspiration level while simultaneously controlling irrigation. For example, multi-purpose valve 562 and fluid lines 549, 50, 54/54', and 52 are configured such that when first flow path 563A is in communication with both irrigation line 50 and irrigation supply line 549, second flow path 563B is only in communication with exhaust line 54/54', leaving aspiration line 52 closed to exhaust line 54/54'. In this arrangement, irrigation is supplied to handpiece 42 and vent line 560 is closed. Alternatively, multi-purpose valve 562 may be rotated slightly from the "irrigation line open, vent line closed" position such that second flow path 563B is open to both aspiration line 52 and exhaust line 54/54', while first flow path 563A is in communication with both irrigation line 50 and irrigation supply line 549. In this configuration, irrigation is being supplied to handpiece 42 and aspiration line 52 is operatively connected to exhaust line 54/54' thereby reducing, if not eliminating aspiration pressure within aspiration line 52. This design effectively eliminates a valve element from system 500, while still providing for selectively varying aspiration pressure and selectively controlling irrigation.

Figure 13:
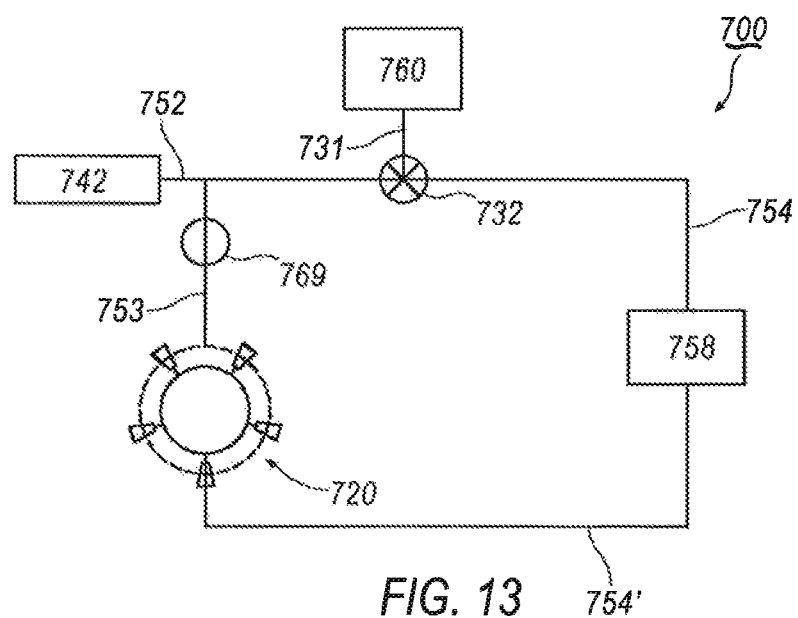
FIG. 13 is a partial schematic diagram of an aspiration circuit for an exemplary arrangement of a phaco fluidics system that employs a multi-aspiration pump system using both venturi and peristaltic pump systems.

Referring now to FIG. 13, a partial schematic of an alternative aspiration circuit 700 for use in a phaco fluidics system is shown. Aspiration circuit 700 employs both displacement-based and/or vacuum-based aspiration modes. Aspiration circuit 700 includes an aspiration line 752 that fluidly connects to handpiece 742 to either an input port 753 of peristaltic pump 720 or an input port 731 of a venturi reservoir 760. Aspiration exhaust lines 754/754' extend from input port 731 of venturi reservoir 760 and input port 753 of peristaltic pump 720, respectively. While prior art configurations used separate valves to close and open input port 731 of venturi reservoir 760 and to provide selective venting of aspiration line 752 to a drain bag 758, aspiration circuit 700 employs a multi-purpose valve 732 that is disposed within a sealed groove of a cassette (similar to that shown in FIG. 12A above) that provides both functions.

Figure 14A:
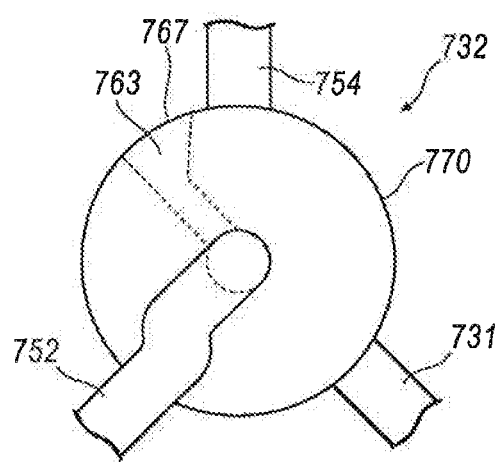
FIG. 14A is a schematic diagram of an exemplary configuration of a multi-purpose valve in a fully open position between the aspiration line and an input port of the pump such that full vacuum pressure is delivered through the aspiration line to the handpiece.
Figure 14B:
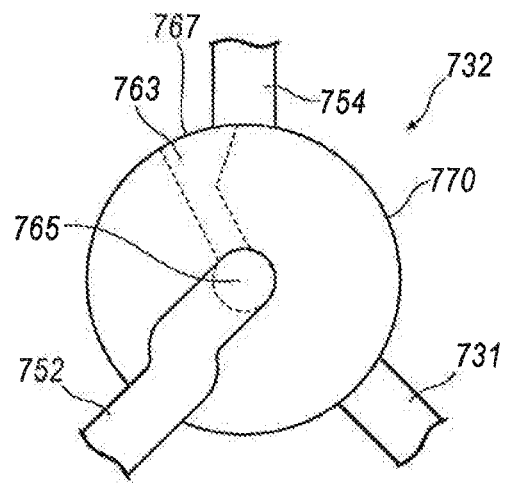
FIG. 14B is a schematic diagram of the multi-purpose valve in a partial open opposition between the aspiration line and the aspiration exhaust line, as well as between the aspiration line and an input port of the pump.
Figure 14C:
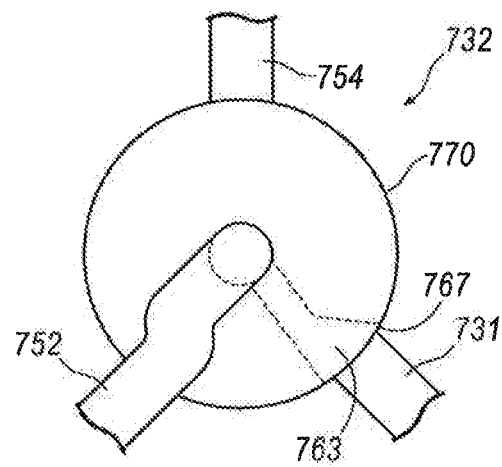
FIG. 14C is a schematic diagram of the multi-purpose valve in a fully open position with the venturi reservoir such that aspiration is directed from same.

More specifically, referring to FIGS. 14A-14C, in one exemplary arrangement multi-purpose valve 732 is configured with a channel 763 that is defined by a first opening 765 and a second opening 767. In one exemplary arrangement, second opening 767 may be configured with an outwardly extending flare. Alternatively, channel 763 may be configured with a triangular shape that flares outwardly toward a periphery 770 of multi-purpose valve 732. First opening 765 is positioned transverse to channel 763. Second opening is formed through a periphery 770 of multi-purpose valve 732.

Referring to FIG. 14A, during operation, multi-purpose valve 732 may be positioned such that aspiration is delivered to aspiration line 752 by pump 720. In this configuration, multi-purpose valve 732 is selectively rotated such that input line 731 to venturi reservoir is closed and aspiration exhaust line 754 is closed off from aspiration line 752. In this configuration, full aspiration is provided by pump 720.

A pressure sensor 769 may be positioned in input line 753 to detect and monitor the pressure in aspiration line 752. Pressure sensor 769 is operably connected to a control system mounted in a console. Pressure sensor 769 detects and communicates pressure changes in aspiration line 752 during operation of the phacoemulsification machine. In one exemplary configuration, predetermined pressure thresholds can be set within the control system such that when pressure readings from pressure sensor 769 exceed those thresholds, the system prompts movement of multi-purpose valve 732 by a predetermined amount to reduce the aspiration pressure within aspiration line 52. More specifically, referring to FIG. 14B, multi-purpose valve 732 may be rotated such that second opening 767 of channel 763 is in at least partial fluid communication with aspiration exhaust line 754. Thus, if pressure has increased within aspiration line 752 by an undesirable amount (such as, for example, because of an occlusion break surge), multi-purpose valve 732 may be selectively moved by a predetermined amount so as to partially open aspiration exhaust line 754, as shown in FIG. 14B. This action quickly and effectively restores the aspiration pressure within aspiration line 752 to the predetermined acceptable amount, without requiring pump reversal. It is understood, however, that channel 763 may be rotated such that aspiration line 752 is fully opened to aspiration exhaust line 754, if need be.

As discussed above, multi-purpose valve 732 may also be used to switch aspiration source from pump 720 to venturi reservoir 760. Referring to FIG. 14C, in this configuration, channel 763 is positioned such that second opening 767 is in communication with input 731 of venturi reservoir 760, thereby connecting aspiration line 752 to venturi reservoir 760. However, aspiration exhaust line 754 is sealed off from aspiration line 752.

In some embodiments, a fluidics system for use in a surgical system may include an aspiration circuit (comprising an aspiration line operatively connected to a surgical instrument, an aspiration exhaust line operatively connected to a waste receptacle, an aspiration vent line connected at a first end to the aspiration line, and a selectively variable valve operatively connected to the aspiration vent line (wherein the variable valve may be selectively actuated to selectively change aspiration pressure within the aspiration line)) and an irrigation circuit (comprising an irrigation source, an irrigation supply line connected to the irrigation source, and an irrigation line having a first end operatively connected to the irrigation supply line and a second end operatively connected to the surgical device). The fluidics system may further include a shunt path, wherein a first end of the shunt path is operatively connected to the irrigation supply line and a second end of the shunt path is connected to the waste receptacle. The fluidics system may further include a selectively positionable irrigation valve that operatively connects the irrigation supply line, the irrigation line, and the shunt path such that the selectively positionable irrigation valve may be moved to direct irrigation from the irrigation supply line. In some embodiments, the irrigation valve may be a rotary valve and include an intersecting channel formed therein, the channel defining a first branch, a second branch, and a third branch. In some embodiments, the irrigation valve is selectively moveable between a first position, a second position and a third position, wherein in the first position, the first branch is positioned in communication with the irrigation supply line and the second branch is positioned in communication with the irrigation line; wherein in the second position, the first branch is positioned in communication with the shunt path and the third branch is in communication with the irrigation supply line; and wherein in the third position, the first branch is positioned in communication with the irrigation line, the second branch is positioned in communication with irrigation supply line and the third branch is positioned in communication with the shunt path. In some embodiments, the variable valve may also be connected to the irrigation line such that the variable valve may be selectively moved to selectively interrupt fluid flow in the irrigation line and to selectively vary aspiration pressure within the aspiration line. In some embodiments, the variable valve may be configured with first and second flow paths formed therein, wherein the first flow path may be selectively aligned with the irrigation supply line and the irrigation line to open the irrigation line to the irrigation supply source, and wherein the second flow path may be selectively aligned with the aspiration line and the aspiration exhaust line to selectively vary aspiration pressure within the aspiration line.

In some embodiments, an aspiration circuit for a fluidics system for selectively controlling aspiration may include an aspiration line operatively connected to a surgical instrument, a first aspiration exhaust line operatively connected to a waste receptacle, a second aspiration exhaust line operatively connected to a waste receptacle, a displacement-based aspiration source operatively connected to the first aspiration exhaust line, a vacuum-based aspiration source operatively connected to the second aspiration exhaust line, and a selectively variable valve operatively connected to both the displacement-based aspiration source and the vacuum-based aspiration source; wherein the variable valve may be actuated to selectively change aspiration pressure within the aspiration line when the displacement-based aspiration source is employed. In some embodiments, the variable valve may be selectively actuated to provide aspiration pressure to the aspiration line from the vacuum-based aspiration source. In some embodiments, the displacement-based aspiration source is a peristaltic pump and the vacuum-based aspiration source includes a venturi reservoir. In some embodiments, the variable valve further comprises a valve body that includes a channel that is defined by a first opening and a second opening, wherein the first opening is positioned transverse to the length of the channel and wherein the second opening is formed through a periphery of the valve body.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. An aspiration circuit for a fluidics system for selectively controlling aspiration, comprising:
   an aspiration line operatively connected to a surgical instrument;
   an aspiration pump to create an aspiration flow in the aspiration line;
   an aspiration exhaust line operatively connected to the aspiration pump on one end and to a waste receptacle on an opposing end;
   an aspiration vent line connected at a first end to the aspiration line between the aspiration pump and the surgical instrument; and
   a selectively variable vent valve operatively connected to the aspiration vent line, wherein the variable vent valve may be selectively moved to selectively change aspiration pressure within the aspiration line;
   an irrigation line operatively connected to the surgical instrument;
   an irrigation pressure sensor and an actuator, the irrigation pressure sensor being positioned to detect irrigation pressure in the irrigation line and the actuator being operatively connected to the vent valve;
   wherein the irrigation pressure sensor and the actuator are connected to a controller, and
   wherein the controller is operative to initiate the actuator to move the vent valve in response to pressure detected by the irrigation pressure sensor to vary the aspiration pressure within the aspiration line.

2. The aspiration circuit of claim 1, wherein the aspiration vent line is connected at a second end to the aspiration exhaust line to form a bypass around the aspiration pump.

3. The aspiration circuit of claim 1, wherein the aspiration vent line is connected at a second end to atmosphere.

4. The aspiration circuit of claim 1, wherein the aspiration vent line is connected at a second end to a vent pressure source of pressurized fluid or saline.

5. The aspiration circuit of claim 1, wherein the aspiration vent line is connected at a second end to an irrigation line.

6. The aspiration circuit of claim 1, further comprising:
   an aspiration pressure sensor and an actuator, the aspiration pressure sensor being operatively connected to the aspiration line and the actuator being operatively connected to the vent valve,
   wherein the aspiration pressure sensor and the actuator are connected to a controller, and
   wherein the controller is operative to initiate the actuator to move the vent valve in response to predetermined pressure values detected by the aspiration pressure sensor to vary the aspiration pressure within the aspiration line.

7. The aspiration circuit of claim 6, wherein the actuator is a motor.

8. The aspiration circuit of claim 6, wherein the controller is operative to move the vent valve by a predetermined amount to reduce the aspiration pressure in the aspiration line wherein a predetermined pressure value is detected.

9. The aspiration circuit of claim 6,
   wherein the controller, using information from the aspiration pressure sensor operatively connected to the aspiration line, is configured to detect an occlusion break onset, and
   wherein the controller is configured to minimize the occlusion break onset by initiating the actuator to move the vent valve.

10. The aspiration circuit of claim 1, wherein the variable vent valve is operatively connected to an irrigation line such that the variable vent valve may be selectively moved so as to selectively interrupt fluid flow in the irrigation line and to selectively vary aspiration pressure within the aspiration line.

11. The aspiration circuit of claim 10, wherein the variable vent valve is configured with first and second flow paths formed therein, wherein the first flow path may be selectively, and at least partially, aligned with an irrigation supply line and the irrigation line to open the irrigation line to an irrigation supply source, and wherein the second flow path may be selectively, and at least partially, aligned with the aspiration line and the aspiration exhaust line to selectively vary the aspiration pressure within the aspiration line.

12. The aspiration circuit of claim 1,
wherein the vent valve is a rotary valve that further comprises an input opening, an output opening and a channel that connects the input opening to the output opening;
wherein the vent valve may be selectively rotated to selectively position the channel in at least partial communication with the aspiration line; and
wherein the vent valve is operably connected to an actuator having an angular position encoder.

13. The aspiration circuit of claim 12, wherein the actuator is configured to move the vent valve to provide a variable orifice size to selectively modulate aspiration within the aspiration line.

14. The aspiration circuit of claim 1, wherein the aspiration pump comprises a series of rollers acting upon an elastomeric sheet defining part of the aspiration line.

15. The aspiration circuit of claim 1, wherein the irrigation pressure sensor is located in the surgical instrument.

16. The aspiration circuit of claim 15, wherein the surgical instrument is a surgical handpiece.

17. The aspiration circuit of claim 1,
wherein the irrigation line provides irrigation fluid to the surgical instrument from an irrigation source; and
wherein the irrigation pressure sensor is located in the irrigation line between the irrigation source and the surgical instrument.

18. The aspiration circuit of claim 1,
wherein the controller, using information from the irrigation pressure sensor, is configured to detect an occlusion break onset, and
wherein the controller is configured to minimize the occlusion break onset by initiating the actuator to move the vent valve.

* * * * *